United States Patent [19]

Lavielle et al.

[11] Patent Number: 4,727,086
[45] Date of Patent: Feb. 23, 1988

[54] CERTAIN ANTI-HYPERTENSIVE 2,3-DIHYDROBENZOFURAN COMPOUNDS

[75] Inventors: Gilbert Lavielle, La Celle Saint-Cloud; Yves-Michel Gargouil, Paris; Jean-Paul Vilaine, Le Plessis Robinson, all of France

[73] Assignee: Adir et Compagnie, Neuilly-sur-Seine, France

[21] Appl. No.: 880,169

[22] Filed: Jun. 30, 1986

[30] Foreign Application Priority Data

Jul. 9, 1985 [FR] France ................ 85 10459

[51] Int. Cl.$^4$ ............... A61K 31/34; C07D 307/81; C07D 307/83
[52] U.S. Cl. ................ 514/463; 514/469; 514/470; 549/433; 549/466; 549/467
[58] Field of Search .............. 549/433, 466, 467; 514/463, 469, 470

[56] References Cited

U.S. PATENT DOCUMENTS 4,602,035  7/1986  Tegeler et al. .............. 549/467

Primary Examiner—Alan L. Rotman
Assistant Examiner—Bernard I. Dentz
Attorney, Agent, or Firm—Gordon W. Hueschen

[57] ABSTRACT

The invention relates to 2,3-dihydrobenzofuran derivatives of the general formula:

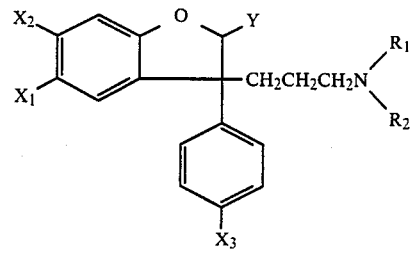

in which:

each of $X_1$ and $X_2$, which are identical or different, represents a hydrogen or halogen atom or an alkoxy radical containing from 1 to 4 carbon atoms, $X_3$ represents a hydrogen atom or an alkyl radical having from 1 to 4 carbon atoms, Y represents a hydrogen atom or a hydroxy radical, each of $R_1$ and $R_2$, which are identical or different, represents an alkyl radical having from 1 to 4 carbon atoms, or $R_1$ represents a methyl radical and $R_2$ represents a phenylalkyl grouping or a 2-indanyl grouping, each of which may be substituted or unsubstituted, or $R_1$ and $R_2$ together form, with the nitrogen atom to which they are attached, a piperazinyl radical, a tetrahydroisoquinolyl radical, a morpholinyl radical or a tetrahydrothienopyridinyl radical. The compounds are useful in the treatment of hypertension.

7 Claims, No Drawings

CERTAIN ANTI-HYPERTENSIVE 2,3-DIHYDROBENZOFURAN COMPOUNDS

The present invention relates to novel 2,3-dihydrobenzofuran derivatives, processes for their preparation and pharmaceutical compositions containing them.

Numerous benzofuran derivatives are known that possess valuable pharmacological properties, especially amiodarone and benziodarone, and that are used in the treatment of angina pectoris. Somewhat surprisingly, the literature mentions few pharmacologically active 2,3-dihydrobenzofuran derivatives. Certain 3-aminoalkyl-2,3-dihydrobenzofuran have been described by Tegeler J. et al. in J. Pharm. Sc. (1985), 74, No. 1, 44-46 and in the Application EP No. 149077 these compounds have a generally low antidepressive activity. Other 3-aminomethyl-2,3-dihydrobenzofurans (U.S. Pat. No. 3,156,688) have exhibited a hypotensive activity in cats in very large doses (25 mg/kg intravenously).

Unlike the compounds of the prior art, the compounds of the present invention and particularly these containing one or several alkoxy radicals, have exhibited very valuable pharmacological properties, especially as modulators of the transmembrane and intracellular movements of calcium.

The present invention relates more especially to the derivatives of 2,3-dihydrobenzofuran of the general formula I:

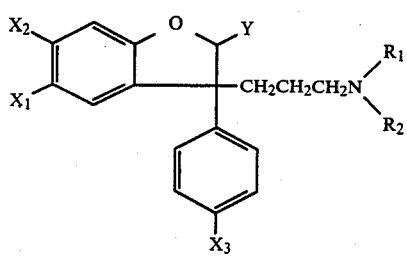

in which:
each of $X_1$ and $X_2$, which are identical or different, represents a hydrogen or halogen atom or an alkoxy radical containing from 1 to 4 carbon atoms, or they together form a methylenedioxy group, $X_3$ represents a hydrogen atom or an alkyl radical, having from 1 to 4 carbon atoms, Y represents a hydrogen atom or a hydroxy radical, each of $R_1$ and $R_2$, which are identical or different, represents an alkyl radical having from 1 to 4 carbon atoms, provided that when Y represents a hydrogen atom, $X_1$ or $X_2$ or $X_1$ and $X_2$ simultaneously, represent an alkoxy radical containing from 1 to 4 carbon atoms, or $R_1$ is a methyl radical and $R_2$ represents a phenylalkyl group containing from 7 to 9 carbon atoms, or a 2-indanyl group, each of which is optionally substituted on the aromatic ring by one or two alkoxy radicals containing from 1 to 4 carbon atoms, provided that $R_2$ never simultaneously represents a phenethyl when $X_1$ and $X_2$ represent a hydrogen or halogen atom and Y represents a hydrogen, or $R_1$ and $R_2$ together form, with the nitrogen atom to which they are attached, a 4-morpholinyl radical, a 1,2,6,7-tetrahydro-(2,3-c)-thieno-1-pyridinyl radical, a 2-tetrahydroisoquinolyl radical optionally substituted by one or two alkoxy radicals having from 1 to 4 carbon atoms, a 4-($C_1$–$C_4$)-alkyl-1-piperazinyl group, or a 4-phenyl-1-piperazinyl group optionally substituted on the aromatic ring by one or two alkoxy radicals containing from 1 to 4 carbon atoms, in racemic form or in the form of optical isomers, and their addition salts with pharmaceutically acceptable mineral or organic acids.

The present invention also relates to the process for the preparation of the compounds of the general formula I, characterised in that a 3-aryl-3-(3-chloropropyl)-2-benzofuranone of the general formula II:

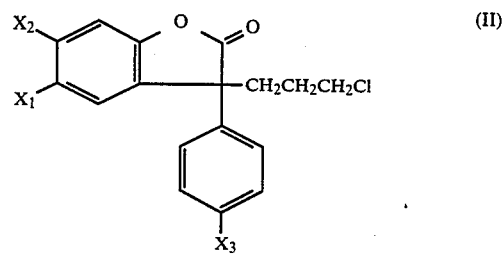

in which the definition of the substituents $X_1$, $X_2$ and $X_3$ is the same as that given above, is condensed with a secondary amine of the general formula III:

in which the definition of $R_1$ and $R_2$ is the same as that given above, to form a derivative of the general formula IV

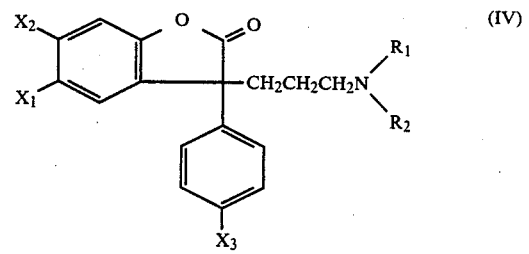

in which $x_1$, $X_2$, $X_3$, $R_1$ and $R_2$ have the meanings defined above for formula I, which is then either partially reduced to form a derivative of the general formula I':

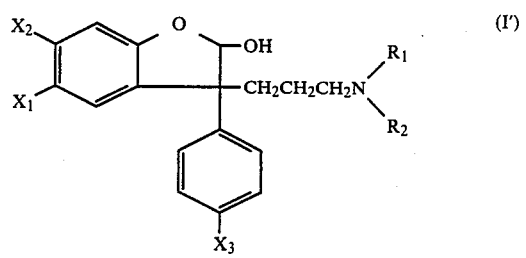

in which $X_1$, $X_2$, $X_3$, $R_1$ and $R_2$ are as defined above, or opened by reduction to form a diol of the general formula V:

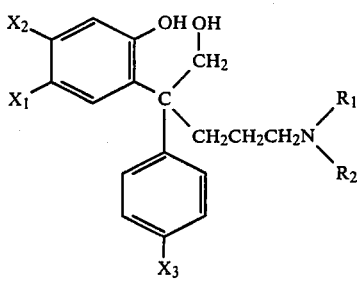

in which $X_1$, $X_2$, $X_3$, $R_1$ and $R_2$ have the meanings defined above for formula I, which is finally cyclised to form a derivative of the general formula I″:

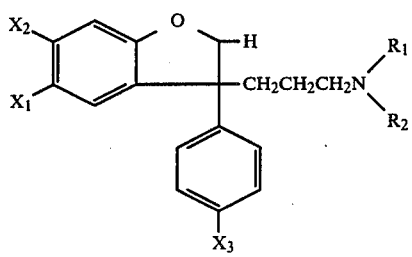

A variant of this process consists in subjecting the 3-aryl-3-(3-chloropropyl)-2-benzofuranone of the general formula II to the action of a reducing agent in order to obtain a diol of the general formula VI:

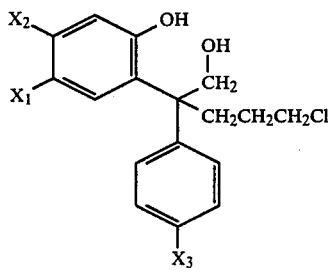

in which the definition of $X_1$, $X_2$ and $X_3$ is the same as that given above in the general formula I, which is then cyclised to form a derivative of the general formula VII:

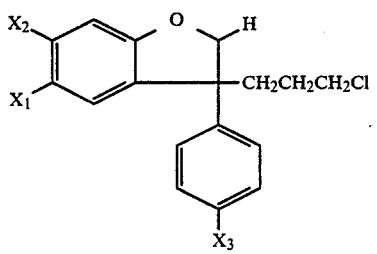

in which $X_1$, $X_2$ and $X_3$ have the meanings defined above for the formula I, which is condensed with an amine of the general formula III in order to obtain a compound of the general formula I″.

All of the compounds of the formulae I′ and I″ form all of the compounds of the formula I which may, if desired, be either converted into their addition salts with pharmaceutically acceptable mineral or organic acids or separated into their optical isomers and then optionally salified using acids.

The starting materials of the general formula II can be prepared according to the method described by Zaugg H. et al. (J. Org. Chem. (1961) 26, 4821–4828).

The condensation of the secondary amines of the general formula III with the compounds of the general formula II or VII is preferably carried out in a polar organic solvent, such as ethanol or methyl ethyl ketone, at a temperature of from 50° C. to 90° C., in the presence of mineral salts, such as sodium carbonate or sodium iodide.

The diols V and VI are obtained by reduction and hydrolysis of the lactones IV and II, respectively. The reduction of the lactones is preferably carried out with the aid of metal hydrides in an inert organic solvent at ambient temperature or at a temperature slightly higher than ambient temperature. More precisely, a metal hydride, such as lithium aluminium hydride, can be used as the reducing agent in tetrahydrofuran.

The partial reduction of the lactones of the general formula IV is carried out in an aprotic organic solvent, for example toluene, at a temperature of from −50° C. to −80° C. in the presence of diisobutylaluminium hydride.

The cyclisation of the alcohol-phenols V and VI is carried out by treating those compounds with butyllithium in an anhydrous inert solvent, such as tetrahydrofuran, and then with an excess of paratoluenesulphonyl chloride, or by using other methods already known in the literature and described by Padwa A., An A., Owens W., in J. Org. Chem. (1978), 43, No. 2, 303–309 and by Gervais C., Anker D., Carret G. and Pacheco H., in Tetrahedron (1979), 33, 745–752.

All the novel derivatives, which form part of this invention, can be purified by physical methods, such as crystallisation or chromatography.

The present invention also relates to the optical isomers of the derivatives corresponding to the general formula I. These isomers can be prepared by resolving the racemic compounds. There may be mentioned as resolving agent, for example, (+) and (−) dibenzoyltartaric acids.

Of the pharmaceutically acceptable acids for the preparation of addition salts of the compounds of the general formula I, there may be mentioned phosphoric, hydrochloric, citric, oxalic, sulphuric, tartaric, maleic acid, etc.

The compounds according to the invention, and also their salts, have very valuable pharmacological properties and are distinguished from the other 2,3-dihydrobenzofuran derivatives already known.

Specifically, pharmacological assays carried out in vitro have shown that these compounds are powerful modulators of the intracellular and transmembrane movements of calcium. Certain cellular activities of smooth or striped muscles, especially their contractility, are associated with the intracytoplasmic concentration of calcium and it has been possible to demonstrate the disturbance of this concentration in certain disorders causing muscular contractility (angor, arterial hypertension, asthma, migraine, oesophagal spasms).

Calcium also plays a part in the regulation of cellular metabolism, especially mitochondrial metabolism, and this metabolism is disturbed in diseases such as cardiac or cerebral ischaemia.

The ability of the compounds of the invention to modulate the movements of calcium therefore permits their use in the treatment of hypertension, angor, asthma, oesophagal spasms, migraine or myocardial and cerebral ischaemia. (Burger's Medicinal Chemistry, 4th Ed. Part III, pp. 54–56, John Wiley and Sons Inc. USA 1981).

The pharmacological assays carried out on dogs have proved in vivo that the activity of the compounds of the invention is at least 20 times greater than that of the other 2,3-dihydrobenzofuran derivatives already known (U.S. Pat. No. 3,156,688) and have thus confirmed their great therapeutic value.

The invention also extends to pharmaceutical compositions that contain as active ingredient at least one compound of the general formula I, one of its isomers or one of its addition salts with a pharmaceutically compatible mineral or organic acid, in association with one or more suitable inert non-toxic excipients.

The pharmaceutical compositions so obtained are advantageously presented in various forms, such as, for example, tablets, dragées, soft gelatine capsules, glossettes or other galenical preparations suitable for sublingual administration, suppositories, or injectable or drinkable solutions.

The dosage may vary widely depending on the age and weight of the patient, the nature and severity of the disorder and also on the mode of administration. The preferred mode of administration is the peroral or parenteral mode. The unit dose will generally range from 1 to 300 mg and the daily dose that can be used in human or animal therapeutics will generally range from 1 to 900 mg. The following examples, which are not intended to be limiting, illustrate the invention.

The melting points indicated are measured according to the micro-Kofler technique. The proton nuclear magnetic resonance spectra (NMR) were generally recorded using $CDCl_3$ as the solvent and TMS as the internal reference. The infra-red spectra are obtained with suspensions of products in Nujol.

EXAMPLE 1

5-methoxy-3-phenyl-3-[3-(N-(3,4-dimethoxyphenethyl)-N-methylamino)-propyl]-2,3-dihydrobenzofuran phosphate (a)

5-methoxy-3-phenyl-3-[3-(N-(3,4-dimethoxyphenethyl)-N-methylamino)-propyl]-2-benzofuranone A mixture containing 16.5 g of 5-methoxy-3-(3-chloropropyl)-2-benzofuranone, prepared according to the method described by Zaugg H. et al. (J. Org. Chem. (1961), 26, 4821–4828), 12.2 g of N-methylhomoveratrylamine, 20 g of sodium carbonate and 1.6 g of sodium iodide in 500 ml of methyl ethyl ketone is heated under reflux, while stirring, for 24 hours. After cooling, the mineral salts are eliminated by filtration and the oily filtrate, after condensation, is taken up in 450 ml of a mixture of water and dichloromethane (1:3). After decanting, the organic phase is recovered and the aqueous phase is extracted again with 300 ml of dichloromethane. The organic phases are collected and evaporated under reduced pressure. 25 g of an oil are obtained which is then chromatographed on a silica column using a solvent gradient (pure dichloromethane, then mixtures of dichloromethane with 5%, 10% and 25% acetone) as the eluant.

After evaporating the solvent, the pure oil obtained (20 g) is used as such in the following stage. Its physical constants are mentioned in Table 1. Yield 75%.

(b)

2-phenyl-2-[(2-hydroxy-5-methoxy)-phenyl]-5-]N-(3,4-dimethoxyphenethyl)-N-methylamino]-1-pentanol 20 g of the lactone obtained above dissolved in 300 ml of tetrahydrofuran are added in small quantities at a temperature of from 25° C. to 35° C. to a suspension of lithium aluminium hydride in 200 ml of tetrahydrofuran. After stirring for 30 minutes, the reaction mixture is hydrolysed in succession, at a temperature of 0° C., with 40 ml of ethanol, 20 ml of water, 40 ml of a 50% sodium hydroxide solution and 60 ml of water. The precipitate formed is eliminated by filtration and the filtrate obtained is concentrated.

17.6 g of a pure oil are obtained the physical constants of which are described in Table 2. Yield 87%.

(c)

5-methoxy-3-phenyl-3-[3-(N-(3,4-dimethoxyphenethyl)-N-methylamino)-propyl]-2,3-dihydrobenzofuran The diol obtained above (15.3 g) is dissolved in 200 ml of anhydrous tetrahydrofuran. 42 ml of a 0.067M solution of butyllithium in hexane are slowly added to this solution at a temperature of 0° C. The reaction temperature is maintained at 10°–15° C. for 30 minutes and then 12.2 g of paratoluenesulphonyl chloride dissolved in 50 ml of tetrahydrofuran are introduced while cooling and stirring. Stirring is continued for two hours at ambient temperature.

The reaction medium is then hydrolysed with 100 ml of water and concentrated under reduced pressure. The residue obtained is taken up in 300 ml of dichloromethane and washed carefully with 10% aqueous sodium carbonate solution and then with water. The organic phase is dried over anhydrous sodium sulphate, concentrated and chromatographed on a silica column. The eluant used is a mixture of ethyl ether, acetone, hexane and methanol (30/20/40/10).

4.8 g of pure oil are thus obtained. Yield 30%.

5-methoxy-3-phenyl-3-[3-(N-(3,4-dimethoxyphenethyl)-N-methylamino)-propyl]-2,3-dihydrobenzofuran phosphate is obtained after the addition of 0.01 mole of phosphoric acid to the oil obtained above and recrystalisation from a mixture of acetone and ethyl ether (20/80).

M.p. = 70° C.

The spectral physical constants of this compound are indicated in Table 3.

EXAMPLES 2a–10a

The following derivatives were prepared according to the process described in Example 1a. Their physical constants are indicated in Table 1.

2a  5-chloro-3-phenyl-3-[3-(4-(3-methoxyphenyl)-1-piperazinyl)-propyl]-2-benzofuranone
Yield 90%

3a  5,6-dimethoxy-3-phenyl-3-[3-(N-(3,4-dimethoxyphenethyl)-N-methylamino)-propyl]-2-benzofuranone
Yield 60%.

4a  5-chloro-3-phenyl-3-[3-(N-(3,4-dimethoxyphenethyl)-N-methylamino)-propyl]-2-benzofuranone
Yield 53%.

5a 5-methoxy-3-(4-methylphenyl)-3-[3-(N-(3,4-dime-thoxyphenethyl)-N-methylamino)-propyl]-2-benzofuranone
Yield 50%.

6a 5-methoxy-3-phenyl-3-[3-(N-(5,6-dimethoxy-2-indanyl)-N-methylamino)-propyl]-2-benzofuranone
Yield 70%.

7a 5-methoxy-3-phenyl-3-[3-(6,7-dimethoxy-1,2,3,4-tetrahydro-2-isoquinolyl)-propyl]-2-benzofuranone
Yield 65%.

8a 5-methoxy-3-phenyl-3-[3-(N-phenethyl-N-methylamino)-propyl]-2-benzofuranone
Yield 70%.

9a 5-methoxy-3-phenyl-3-[3-(4-methyl-1-piperazinyl)-propyl]-2-benzofuranone
Yield 75%.

10a 5-methoxy-3-phenyl-3-[3-(N-diethylamino)-propyl]-2-benzofuranone
Yield 80%.

EXAMPLES 2b-10b

The following compounds were prepared according to the process described in Example 1b, starting from the corresponding 2-benzofuranones described above. The spectral physical constants of these alcohols are indicated in Table 2.

2b 2-phenyl-2-[(2-hydroxy-5-chloro)-phenyl]-5-[4-(3-methoxyphenyl)-1-piperazinyl]-1-pentanol
M.p.=120° C.
Yield 98%.

3b 2-phenyl-2-[(2-hydroxy-4,5-dimethoxy)-phenyl]-5-[N-(3,4-dimethoxyphenethyl)-N-methylamino]-1-penttanol
Yield 40%.

4b 2-phenyl-2-[(2-hydroxy-5-chloro)-phenyl]-5-[N-(3,4-dimethoxyphenethyl)-N-methylamino]-pentanol
Yield 70%.

5b 2-(4-methylphenyl)-2-[(2-hydroxy-5-methoxy)-phenyl]-5-[N-(3,4-dimethoxyphenethyl)-N-methylamino]-1-pentanol
Yield 95%.

6b 2-phenyl-2-[(2-hydroxy-5-methoxy)-phenyl]-5-[N-(5,6-dimethoxy-2-indanyl)-N-methylamino]-1-pentanol
Yield 90%.

7b 2-phenyl-2-[(2-hydroxy-5-methoxy)-phenyl]-5-(6,7-dimethoxy-1,2,3,4-tetrahydro-2-isoquinolyl)-1-pentanol
Yield 60%.

8b 2-phenyl-2-[(2-hydroxy-5-methoxy)-phenyl]-5-(N-phenethyl-N-methylamino)-1-pentanol
Yield 70%.

9b 2-phenyl-2-[(2-hydroxy-5-methoxy)-phenyl]-5-(4-methyl-1-piperazinyl)-1-pentanol
Yield 65%.

10b 2-phenyl-2-[(2-hydroxy-5-methoxy)-phenyl]-5-(N-diethylamino)-1-pentanol
Yield 90%.

EXAMPLES 2-10

The following 2,3-dihydrobenzofurans (Examples 2-10) were prepared by cyclising compounds 2b-10b according to the process described in Example 1c. Their spectral physical constants are indicated in Table 3.

2 5-chloro-3-phenyl-3-[3-(4-(3-methoxyphenyl)-1-piperazinyl)-propyl]-2,3-dihydrobenzofuran
Yield 30%
Melting point of the oxalate: 140° C.

3 5,6-dimethoxy-3-phenyl-3-[3-(N-(3,4-dimethoxyphenethyl)-N-methylamino)-propyl]-2,3-dihydrobenzofuran
Yield 50%
Melting point of the phosphate: 94° C.

4 5-chloro-3-phenyl-3-[3-(N-(3,4-dimethoxyphenethyl)-N-methylamino)-propyl]-2,3-dihydrobenzofuran
Yield 52%
Melting point of the hydrochloride: 95° C.

5 5-methoxy-3-(4-methylphenyl)-3-[3-(N-(3,4-dimethoxyphenethyl)-N-methylamino)-propyl]-2,3-dihydrobenzofuran
Yield 50%.
Melting point of the phosphate: 84° C.

6 5-methoxy-3-phenyl-3-[3-(N-(5,6-dimethoxy-2-indanyl)-N-methylamino)-propyl]-2,3-dihydrobenzofuran
Yield 40%
Melting point of the phosphate 110° C.

7 5-methoxy-3-phenyl-3-[3-(6,7-dimethoxy-1,2,3,4-tetrahydro-2-isoquinolyl)-propyl]-2,3-dihydrobenzofuran
Yield 60%
Melting point of the phoshpate: 106° C.

8 5-methoxy-3-phenyl-3-[3-(N-phenethyl-N-methylamino)-propyl]-2,3-dihydrobenzofuran
Yield 55%
Melting point of the phosphate: 75° C.

9 5-methoxy-3-phenyl-3-[3-(4-methyl-1-piperazinyl)-propyl]-2,3-dihydrobenzofuran
Yield 55%
Melting point of the hydrochloride: 175° C.

10 5-methoxy-3-phenyl-3-[3-(N-diethylamino)-propyl]-2,3-dihydrobenzofuran
Yield 30%
Melting point of the hydrochloride: 146° C.

EXAMPLE 11

2-Hydroxy-5-methoxy-3-phenyl-3-[3-(N-(3,4-dimethoxyphenethyl)-N-methylamino)-propyl]-2,3-dihydrobenzofuran phosphate 11a
2-hydroxy-5-methoxy-3-phenyl-3-[3-(N-(3,4-dimethoxyphenethyl)-N-methylamino)-propyl]-2,3-dihydrobenzofuran 41 ml of a molar solution of diisobutylaluminium hydride in toluene are added slowly, while stirring, to a solution of 200 ml of toluene that has been cooled to −80° C. and contains 4.6 g of the lactone obtained above in Example 1a. The reaction mixture is left for 3 hours at −80° C. while stirring and then 80 ml of a 2M solution of isopropanol in toluene are added while allowing the temperature to rise and reach 0° C. 8 ml of water and 20 g of fine silica are then introduced into the reaction medium. After filtration over silica and concentration, the residue is taken up in 300 ml of dichloromethane, washed with water, dried over anhydrous sodium sulphate and concentrated again. 3.3 g of pure oil are thus obtained.
Yield 70%.

2-hydroxy-5-methoxy-3-phenyl-3-[3-(N-(3,4-dimethoxyphenethyl)-N-methylamino)-propyl]-2,3-dihydrobenzofuran phosphate is prepared by the addition of an equimolar amount of phosphoric acid and recrystallization from a mixture of ethyl ether and acetone (95/5).

The spectral physical constants of the compound are indicated in Table 3.

M.p. = 108° C.

EXAMPLE 12

2-hydroxy-5,6-dimethoxy-3-phenyl-3-[3-(N-(3,4-dimethoxyphenethyl)-N-methylamino)-propyl]-2,3-dihydrobenzofuran phosphate This compound is prepared starting from the lactone of Example 3a and according to the process described in Example 11.

Yield 40%. Its spectral physical constants are indicated in Table 3.

M.p. = 100° C.

EXAMPLE 13

3-phenyl-3-[3-(N-(3,4-dimethoxyphenethyl)-N-methylamino)-propyl]-2,3-dihydrobenzofuran phosphate 13a 2-phenyl-2-(2-hydroxyphenyl)-5-chloro-1-pentanol 250 ml of an ethyl ether solution containing 40 g of aluminium chloride, and then a mixture containing 40 g of 3-(3-chloropropyl)-2-benzofuranone and 18.6 g of aluminium chloride in 1 liter of ethyl ether are added very slowly in succession and at ambient temperature to a suspension of lithium aluminium hydride in 250 ml of ether.

The reaction medium is left for 1 hour while stirring and is then poured onto 1.5 liters of glacial 1N hydrochloric acid. After extraction with 500 ml of ether, the organic phase is recovered, washed with 500 ml of a saturated aqueous sodium chloride solution, dried over anhydrous sodium sulphate and evaporated. The residue is recrystallised from a mixture of petroleum ether and ethyl ether (70/30).

28.5 g of alcohol are obtained.

Yield 70%

M.p. = 119° C.

proton NMR spectrum: 1.2 to 1.9 ppm m 2H; 2.1 to 2.6 ppm m 3H and 1H exchangeable; 3.4 ppm t 2H; 4.1 ppm q 2H; 6.45 ppm 1H exchangeable; 6.6 to 7.6 ppm m 9H.

13b 3-phenyl-3-(3-chloropropyl)-2,3-dihydrobenzofuran 0.051 mole of butyllithium dissolved in 31.9 ml of hexane is added very slowly to 7 g of the diol obtained above which had been cooled to a temperature of −80° C. The reaction proceeds for 30 minutes at a temperature of −80° C. and then for 15 minutes at a temperature of −65° C. The reaction solution is then cooled to −80° C. and 6.95 g of paratoluenesulphonyl chloride dissolved in 80 ml of tetrahydrofuran are added. The temperature is slowly increased to 25° C. The reaction medium is left for 1 hour while stirring and then hydrolysed with 110 ml of a 4N sodium hydroxide solution. After two hours' contact, the solution is concentrated and the residue is recovered from ethyl ether. The organic phase is washed with water, dried over anhydrous sodium sulphate and concentrated. The oil obtained is purified on a silica column by elution with 1.5 liters of a mixture of ethyl ether and hexane (10/90). 5.3 g of 3-phenyl-3-(3-chloropropyl)-2,3-dihydrobenzofuran are thus obtained.

Yield 80%.

proton NMR spectrum: 1.5 to 1.9 ppm m 2H; 2.2 to 2.3 ppm m 2H; 3.48 ppm t 2H; 4.53 ppm s 2H; 6.8 to 7.4 ppm m 9H.

13c.

3-phenyl-3-[3-(N-(3,4-dimethoxyphenethyl)-N-methylamino)-propyl]-2,3-dihydrobenzofuran 5.2 g of the compound obtained above in Example 15b are heated under reflux for 4 hours in 250 ml of methyl ethyl ketone in the presence of 4.5 g of N-methylhomoveratrylamine, 8 g of sodium carbonate and 0.5 g of sodium iodide.

After eliminating the mineral salts by filtration, the reaction medium is concentrated, taken up in 150 ml of a 10% aqueous sodium carbonate solution and then extracted with benzene.

The organic phase is dried over anhydrous sodium sulphate and concentrated and the residue obtained is purified on a silica column under pressure. After elution with a mixture of dichloromethane, acetone and methanol (67/30/3) 5.4 g of pure product are obtained.

Yield 50%.

3-phenyl-3-[3-(N-(3,4-dimethoxyphenethyl)-N-methylamino)-propyl]-2,3-dihydrobenzofuran phosphate is obtained after the addition of an appropriate amount of phosphoric acid to the base obtained in Example 13c. The salt was purified by crystallisation from a mixture of ethyl ether and ethanol (95/5). The spectral physical constants of the compound are described in Table 3.

M.p. = 70° C.

EXAMPLES 14–16

The following compounds (Examples 14–16) are obtained by condensing 3-phenyl-3-(3-chloropropyl)-2,3-dihydrobenzofuran (Example 13b) with appropriate secondary amines according to the process described in Example 13c. The spectral physical constants of compounds 14–16 are indicated in Table 3.

14    3-phenyl-3-[3-(1,2,6,7-tetrahydro-(2,3-c)-thieno-1-pyridinyl)-propyl]-2,3-dihydrobenzofuran Yield 70%

Melting point of the citrate: 90° C.

15    3-phenyl-3-[3-(4-morpholinyl)-propyl]-2,3-dihydrobenzofuran

Yield 40%

Melting point of the hydrochloride: 200° C.

16  3-phenyl-3-[3-(4-(3-methoxyphenyl)-1-piperazinyl)-propyl]-2,3-dihydrobenzofuran Yield 40%

Melting point of the hydrochloride: 171° C.

The spectral physical constants of these compounds are described in Table 3.

Pharmacological Study of the Compounds of the Invention

EXAMPLE 17

Assessment of the Contraction-Inhibiting Activity on the Coronary Artery of the Dog The inhibiting activity on contraction induced by calcium ions was assessed in vitro on the coronary artery of the dog according to the method described by Godfraind and Miller in Circ. Res. (1983) 52, No. 2, pp. 81–91. Contraction was induced by a solution containing 100 millimoles of potassium ions per liter. The compounds to be examined were then introduced in cumulative doses and after a 15-minute period of action the preparation was reactivated with solutions having a calcium ion concentration of 10 and 20 mM. The dose capable of inhibiting 50% ($ED_{50}$) of the maximum contraction was assessed. The measured $ED_{50}$'s of the various compounds are indicated in Table 4 (see Table below).

TABLE 4

| COMPOUNDS OF EXAMPLE | $ED_{50}$ (M) |
|---|---|
| 1 | $1.7 \times 10^{-6}$ |
| 2 | $1.0 \times 10^{-5}$ |
| 3 | $9.0 \times 10^{-5}$ |
| 4 | $3.0 \times 10^{-5}$ |
| 5 | $2.6 \times 10^{-5}$ |
| 6 | $1.0 \times 10^{-5}$ |
| 7 | $6.3 \times 10^{-6}$ |
| 8 | $8.4 \times 10^{-6}$ |
| 9 | $3.5 \times 10^{-5}$ |
| 10 | $6.1 \times 10^{-6}$ |
| 11 | $6.2 \times 10^{-6}$ |
| 12 | $8.0 \times 10^{-6}$ |
| 13 | $4.0 \times 10^{-6}$ |
| 14 | $9.0 \times 10^{-6}$ |
| 15 | $5.0 \times 10^{-5}$ |
| 16 | $9.0 \times 10^{-6}$ |

EXAMPLE 18

Assessment of the Contraction-Inhibiting Activity on the Caudal Artery of the Rat The contraction-inhibiting activity on the vessels was measured in vitro on the caudal artery of male Wistar rats. The artery was perfused at a constant rate and denervated beforehand with a solution of 6-hydroxydopamine. When vasoconstriction had been induced by a 90 mM potassium ion solution, the pressure of the perfusion liquid at the entrance to the artery was measured before and after the addition in cumulative doses of the compounds to be examined, according to the method described by Worcel M. in J. Pharmacol. Exp. Ther., (1978), 207, 320–330. The dose capable of inhibiting 50% ($ED_{50}$) of the maximum contraction was evaluated. The $ED_{50}$'s of the compounds of the invention are from $1 \times 10^{-5}$ to $1 \times 10^{-6}$ M.

EXAMPLE 19

Assessment of the Contraction- and Rhythm-Inhibiting Activity on the Auricle of the Rat The contraction- and rhythm-inhibiting activity was assessed in vitro on the isolated left auricle of male albino Wistar rats according to the method described by Refsum H. and Landmark K. in Acta Pharmacol. (1975), 37, 369–379. The organ was subjected to electrical stimulation using bipolar platinum electrodes, with pulses lasting 0.5 msec, at a frequency of 3 Hz. The initial tension applied (500 mg) corresponded to the maximum contraction. The isometric contraction and the rhythm were measured before and after the addition, in cumulative doses, of the compounds to be examined. The dose capable of inhibiting 50% ($ED_{50}$) of the maximum contraction was evaluated. The $ED_{50}$'s of the compounds of the invention are from $1 \times 10^{-5}$ to $1 \times 10^{-4}$ M.

EXAMPLE 20

Haemodynamic Effects In Vivo

The haemodynamic effects were assessed in mongrel dogs weighing from 25 to 30 kg which had been anaesthetised with sodium phenobarbital, had undergone a thoractomy at the 5th left intercostal space and carried electromagnetic rings at the level of the circumflex branch of the left coronary artery and at the level of the ascending aorta. The maximum bradycardic effect (E.B. max.), the mean coronary resistances (C.V.R.M.), the coronary output (C.B.F.M.), and the arterial pressure (P.A.) were measured after the intravenous injection of a dose of 300 µg/kg and 1000 µg/kg of the compounds of Examples 1 and 13.

Table 5 summarises the various results which are expressed as percentage increases (+%) or percentage decreases (−%) in the values in relation to those observed before treatment.

TABLE 5

| Compounds of Example | Dose | EB max | CRVM | CBFM | PA |
|---|---|---|---|---|---|
| Example 1 (phosphate) | 300 µg/kg | −7% | −39% | +51% | −9% |
| | 1000 µg/kg | −13% | −57% | +85% | −21% |
| Example 13 (phosphate) | 300 µg/kg | −8% | −36% | +31% | −16% |
| | 1000 µg/kg | −10% | −60% | +59% | −31% |

PHARMACEUTICAL PREPARATION

The following pharmaceutical preparation is given by way of a non-limiting example.

| 5-methoxy-3-phenyl-3-[3-(N—(3,4-dimethoxyphenethyl)- N—methylamino)-propyl]-2,3-dihydrobenzofuran phosphate, expressed in: | |
|---|---|
| base | 25.00 g |
| wheat starch | 100.00 g |
| corn starch | 80.00 g |
| magnesium stearate | 15.00 g |
| talc | 20.00 g | for 1000 tablets each containing 25 mg of active ingredient.

TABLE 1

| | | | | COMPOUNDS OF THE GENERAL FORMULA IV | | | |
|---|---|---|---|---|---|---|---|
| EX | $X_1$ | $X_2$ | $X_3$ | $R_1$ | $R_2$ | IR $\nu$(CO) lactone | NMR |
| 1a | —$OCH_3$ | —H | —H | —$CH_3$ | 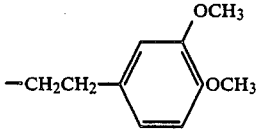 | 1800 cm$^{-1}$ | 0.8 to 2 ppm m 2H; 2 to 3 ppm m 8H; 2.2 ppm s 3H; 3.9 ppm s 9H; 6.5 to 7.5 ppm m 11H. |
| 2a | —Cl | —H | —H | | 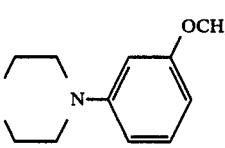 | 1810 cm$^{-1}$ | 1.4 ppm m 2H; 2 to 2.8 ppm m 6H; 2.8 to 3.4 ppm m 4H; 3.7 ppm s 3H; 6.2 to 7.6 ppm m 12H. |

TABLE 1-continued

COMPOUNDS OF THE GENERAL FORMULA IV

| EX | $X_1$ | $X_2$ | $X_3$ | $R_1$ | $R_2$ | IR $\nu$(CO) lactone | NMR |
|---|---|---|---|---|---|---|---|
| 3a | —OCH$_3$ | —OCH$_3$ | —H | —CH$_3$ | —CH$_2$CH$_2$—(3,4-dimethoxyphenyl) | 1790 cm$^{-1}$ | 1.0 to 1.8 ppm m 2H; 2 to 3 ppm m 11H; 3.9 to 3.95 ppm s 12H; 6.8 ppm m 5H; 7.4 ppm m 5H. |
| 4a | —Cl | —H | —H | —CH$_3$ | —CH$_2$CH$_2$—(3,4-dimethoxyphenyl) | 1805 cm$^{-1}$ | 1 to 2 ppm m 2H; 2 to 3 ppm m 11H; 3.9 ppm s 6H; 6.5 to 7.6 ppm m 11H. |
| 5a | —OCH$_3$ | —H | —CH$_3$ | —CH$_3$ | —CH$_2$CH$_2$—(3,4-dimethoxyphenyl) | 1800 cm$^{-1}$ | 1.1 to 1.5 ppm m 2H; 2.1 to 2.7 ppm m 8H; 2.1 ppm s 3H; 2.3 ppm s 3H; 3.75 ppm s 9H; 6.7 to 7.4 ppm m 10H. |
| 6a | —OCH$_3$ | —H | —H | —CH$_3$ | (5,6-dimethoxyindan-2-yl) | 1800 cm$^{-1}$ | 1 to 4 ppm m 14H; 3.9 s 9H; 6.5 to 7.8 m 10H. |
| 7a | —OCH$_3$ | —H | —H | | (6,7-dimethoxy-1,2,3,4-tetrahydronaphthalen-2-yl) | 1790 cm$^{-1}$ | 1 to 2 ppm m 2H; 2 to 3 ppm m 8H; 3.4 ppm s 2H; 3.8 ppm s 9H; 6.4 to 7.6 ppm m 10H. |
| 8a | —OCH$_3$ | —H | —H | —CH$_3$ | —CH$_2$CH$_2$—phenyl | 1790 cm$^{-1}$ | 1 to 1.5 ppm m 2H; 2 to 2.8 ppm m 11H; 3.8 ppm s 3H; 6.5 to 7.5 ppm m 13H. |
| 9a | —OCH$_3$ | —H | —H | | N-methylpiperidin-4-yl | 1800 cm$^{-1}$ | (hydrochloride) 1 to 3 ppm m 4H; 2.8 ppm s 11H; 3.8 ppm s 3H; 3.8 ppm s 3H; 6.7 to 7.8 ppm m 8H; 11 to 13 ppm 2H exchangeable |
| 10a | —OCH$_3$ | —H | —H | —C$_2$H$_5$ | —C$_2$H$_5$ | 1800 cm$^{-1}$ | 0.8 to 2 ppm m 8H; 2 to 2.6 ppm m 8H; 3.8 ppm s 3H; 6.7 to 7.5 ppm m 8H. |

TABLE 2

COMPOUNDS OF THE GENERAL FORMULA V

| EX | $X_1$ | $X_2$ | $X_3$ | $R_1$ | $R_2$ | IR $\nu$(OH) | NMR |
|---|---|---|---|---|---|---|---|
| 1b | —OCH$_3$ | —H | —H | —CH$_3$ | —CH$_2$CH$_2$—(3,4-dimethoxyphenyl) | 3600–2300 cm$^{-1}$ | 1 to 3 ppm m 4H; 2.4 ppm s 3H; 2.8 ppm m 6H; 3.8 to 3.9 ppm m 9H; 3.9 ppm q 2H; 6.2 ppm 2H exchangeable; 6.8 to 7.35 ppm m 11H. |
| 2b | —Cl | —H | —H | | (3-methoxyphenyl)piperidinyl | 3600–2300 cm$^{-1}$ | 1.3 to 2.5 ppm m 4H; 2.7 to 4.3 ppm m 10H; 3.8 ppm s 3H; 4 ppm q 2H; 6.4 ppm 2H exchangeable; 6.3 to 7.4 ppm 12H. |
| 3b | —OCH$_3$ | —OCH$_3$ | —H | —CH$_3$ | —CH$_2$CH$_2$—(3,4-dimethoxyphenyl) | 3600–2300 cm$^{-1}$ | 1 to 3 ppm m 4H; 2.4 ppm s 3H; 2.8 ppm m 6H; 3.8 to 3.9 ppm m 12H; 3.9 ppm q 2H; 6.2 ppm 2H exchangeable. 6.8 to 7.9 ppm m 10H. |

TABLE 2-continued

| | | | COMPOUNDS OF THE GENERAL FORMULA V | | | |
|---|---|---|---|---|---|---|
| EX | X₁ | X₂ | X₃ | R₁ | R₂ | IR ν(OH) | NMR |
| 4b | —Cl | —H | —H | —CH₃ | 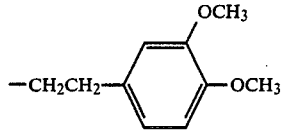 | 3700–2300 cm⁻¹ | 0.8 to 1.5 ppm m 2H; 1.3 to 3 ppm m 11H; 3 ppm s 6H; 3 to 4.5 ppm m 2H; 6 to 7.5 ppm m 11H and 2H exchangeable. |
| 5b | —OCH₃ | —H | —CH₃ | —CH₃ | 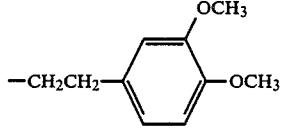 | 3700–2300 cm⁻¹ | 1 to 2 ppm m 2H; 2 to 3 ppm m 14H; 3.6 to 3.86 ppm m 9H; 4.2 ppm q 2H; 6 to 7.5 ppm m 10H and 2H exchangeable. |
| 6b | —OCH₃ | —H | —H | —CH₃ | 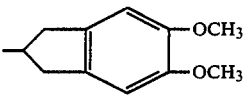 | 3700–2300 cm⁻¹ | 1.7 ppm m 4H; 2.2 ppm s 3H; 2.3 to 3.7 ppm m 7H; 3.5 ppm s 3H; 3.8 ppm s 6H; 4.2 ppm q 2H; 6.0 to 7.3 ppm m 10H and 2H exchangeable. |
| 7b | —OCH₃ | —H | —H | | 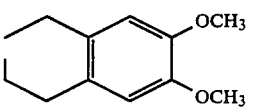 | 3600–2300 cm⁻¹ | 1 to 2 ppm m 2H; 2 to 3 ppm m 8H; 3.5 ppm s 2H; 3.6 ppm s 3H; 3.85 ppm s 6H; 4.2 ppm q 2H; 5.2 to 6.2 ppm 2H exchangeable. 6.2 to 6.8 ppm m 5H; 7.3 ppm m 5H. |
| 8b | —OCH₃ | —H | —H | —CH₃ | —CH₂CH₂—⟨phenyl⟩ | 3600–2300 cm⁻¹ | 1 to 2 ppm m 2H; 2 to 3.2 ppm m 11H; 3.6 ppm s 3H; 4.15 ppm q 2H; 6.2 to 7.6 ppm m 13H and 2H exchangeable. |
| 9b | —OCH₃ | —H | —H | | 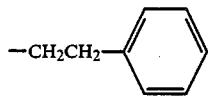 | 3600–2600 cm⁻¹ | 1.3 to 2.4 ppm m 4H; 2.3 ppm s 3H; 2.5 to 2.8 ppm m 10H; 3.9 ppm s 3H; 4.22 ppm q 2H; 6.5 to 7.3 ppm m 8H and 2H exchangeable. |
| 10b | —H | —H | —H | —C₂H₅ | —C₂H₅ | 3600–2400 cm⁻¹ | 0.8 to 2 ppm m 8H; 2 to 2.6 ppm m 8H; 3.8 ppm s 3H; 4.1 ppm q 2H; 6.4 to 7.5 ppm m 8H and 2H exchangeable. |

TABLE 3

| | | | COMPOUNDS OF THE GENERAL FORMULA I | | | | |
|---|---|---|---|---|---|---|---|---|
| EX | X₁ | X₂ | X₃ | R₁ | R₂ | Y | IR (NH)* | NMR |
| 1 | OCH₃ | H | H | CH₃ | 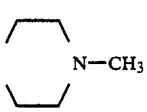 | H | (phosphate) 3500–2000 cm⁻¹ | (phosphate) 1.9 to 2.3 ppm m 2H; 2.4 to 3.1 ppm m 11H; 3.5 to 3.9 ppm m 9H; 4.4 ppm s 2H; 6.6 to 7.2 ppm m 11H; 9 to 9.6 ppm exchangeable protons. |
| 2 | Cl | H | H | | 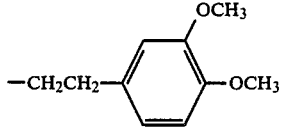 | H | (oxalate) 3000–2000 cm⁻¹ | (oxalate) 1.3 to 2.5 ppm m 4H; 2.7 to 3.5 ppm m 10H; 3.7 ppm s 3H; 4.5 ppm s 2H; 6.3 to 7.5 ppm m 11H; 9.8 ppm 2H exchangeable. |
| 3 | OCH₃ | OCH₃ | H | CH₃ | 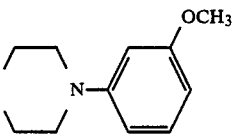 | H | (phosphate) 3500–2000 cm⁻¹ | (base) 1 to 2 ppm m 2H; 1.8 to 2.8 ppm m 11H; 3.8 to 3.9 ppm m 12H; 4.5 ppm s 2H; 6.5 to 7 ppm m 5H; 7.3 ppm m 5H. |
| 4 | Cl | H | H | CH₃ | 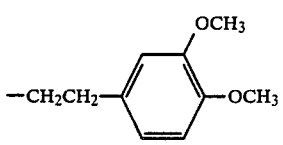 | H | (hydrochloride) 3500–2000 cm⁻¹ | (hydrochloride) 1 to 2 ppm m 2H; 2 to 3.2 ppm m 11H; 3.9 ppm s 6H; 4.55 ppm s 2H; 6.7 to 7.5 ppm m 11H. |

TABLE 3-continued

COMPOUNDS OF THE GENERAL FORMULA I

| EX | $X_1$ | $X_2$ | $X_3$ | $R_1$ | $R_2$ | Y | IR (NH)* | NMR |
|---|---|---|---|---|---|---|---|---|
| 5 | $OCH_3$ | H | $CH_3$ | $CH_3$ | 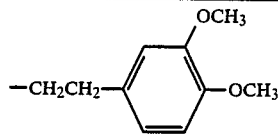 | H | (phosphate) 3700–2000 cm$^{-1}$ | (phosphate) 1 to 2 ppm m 2H; 1.3 to 2.8 ppm m 14H; 3.85 ppm s 3.95 ppm s 6H; 4.5 ppm s 2H; 6.5 to 7.5 ppm m 10H. |
| 6 | $OCH_3$ | H | H | $CH_3$ | 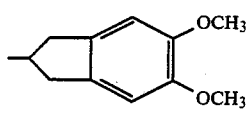 | H | (phosphate) 3600–2000 cm$^{-1}$ | (phosphate) 2 to 3 ppm m 14H; 3.5 ppm s 6H; 3.6 ppm s 6H; 4.3 ppm s 2H; 6.5 to 7.3 ppm m 10H. |
| 7 | $OCH_3$ | H | H | | 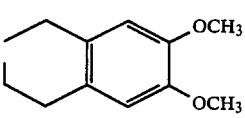 | H | (phosphate) 3600–2000 cm$^{-1}$ | (phosphate) 1.3 to 3.5 ppm m 10H; 3.5 to 4 ppm m 11H; 4.5 s 2H; 6 to 7.5 ppm m 10H; 9.7 ppm H exchangeable. |
| 8 | $OCH_3$ | H | H | $CH_3$ | 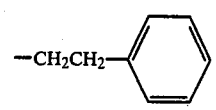 | H | (phosphate) 37000– 2000 cm$^{-1}$ | (phosphate) 1 to 2.5 ppm m 2H; 2.5 to 3.5 ppm m 11H; 3.6 ppm s 3H; 4.5 ppm s 2H; 6.5 to 7.6 ppm m 13H; 9.4 ppm H exchangeable. |
| 9 | $OCH_3$ | H | H | | 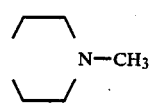 | H | (hydrochloride) 3600–2150 cm$^{-1}$ | (hydrochloride) 1.5 to 2.5 ppm m 4H; 3 ppm s 3H; 3.8 ppm 2H exchangeable; 3.8 ppm t 10H; 3.9 ppm s 3H; 4.6 ppm s 2H; 6.9 to 7.5 ppm m 8H. |
| 10 | $OCH_3$ | H | H | $C_2H_5$ | $-C_2H_5$ | H | (hydrochloride) 2500 cm$^{-1}$ | (hydrochloride) 1.3 ppm t 6H; 2.1 ppm m 4H; 3 ppm m 6H; 3.8 ppm s 3H; 4.6 ppm s 2H; 6.8 ppm 3H 7.4 ppm m 5H; 11 ppm H exchangeable. |
| 11 | $OCH_3$ | H | H | $CH_3$ |  | OH | (base) 3500–3400 cm$^{-1}$ | 1.4 ppm m 2 H; 11H; 2.2 to 2.8 ppm m 3.7 to 4 ppm m 9H; 5.8 ppm s 1H 6.4 to 6.9 ppm m 6H; 7.3 ppm m 5H and H exchangeable. |
| 12 | $OCH_3$ | $OCH_3$ | H | $CH_3$ | 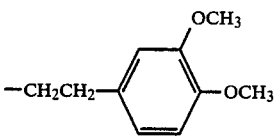 | OH | (base) 3500–3400 cm$^{-1}$ | (base) 1.4 ppm m 2H; 2.2 to 2.8 ppm m 11H; 3.4 to 4 ppm m 12H; 5.8 ppm s 1H; 6.4 to 6.9 ppm m 5H; 7.3 ppm m 5H and H exchangeable. |
| 13 | H | H | H | $CH_3$ | 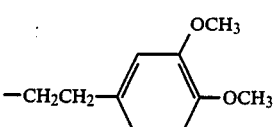 | H | (phosphate) 3700–2200 cm$^{-1}$ | (phoshate) 1 to 2.5 ppm m 2H; 2.5 to 3.5 ppm m 11H; 3.7 ppm s 6H; 4.5 ppm m 2H; 6.5 to 7.7 ppm m 12H; 10.1 ppm H exchangeable. |
| 14 | H | H | H | | 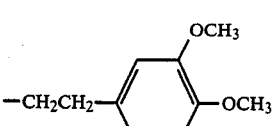 | H | (citrate) 3600–2000 cm$^{-1}$ | (citrate) 1 to 2.5 ppm m 6H; 2.5 to 3.5 ppm m 8H; 3.55 ppm s 2H; 4.55 ppm s 2H; 6.5 to 7.6 ppm m 11H; 8.2 ppm 4H exchangeable. |
| 15 | H | H | H | | 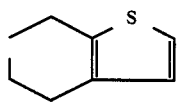 | H | (hydrochloride) 2100–2700 cm$^{-1}$ | (base) 1 to 1.8 ppm m 10H; 3.5 to 3.8 ppm m 4H; 4.5 ppm s 2H; 6.7 to 7.6 ppm m 9H. |
| 16 | H | H | H | | 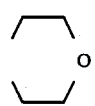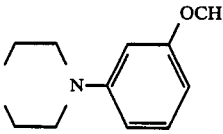 | H | (hydrochloride) 2100–2700 cm$^{-1}$ | (hydrochloride) 1.5 to 2.5 ppm m 4H; 2.7 to 4.3 ppm m 10H; 3.8 ppm s 3H; 4.5 ppm s 2H; 6.5 to 7.5 ppm m 13H; 13 ppm H exchangeable |

We claim:
1. A compound of the formula I:

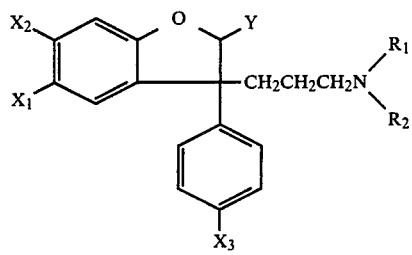

in which:
- each of $X_1$ and $X_2$, which are identical or different, represents a hydrogen or halogen atom or an alkoxy radical containing from 1 to 4 carbon atoms, or they together form a methylenedioxy radical,
- $X_3$ represents a hydrogen atom or an alkyl radical having from 1 to 4 carbon atoms,
- Y represents a hydrogen atom or a hydroxy radical,
- each of $R_1$ and $R_2$, which are identical or different, represents an alkyl radical having from 1 to 4 carbon atoms, provided that when Y represented a hydrogen atom, $X_1$ or $X_2$ or $X_1$ and $X_2$ simultaneously represent an alkoxy radical containing from 1 to 4 carbon atoms,
- or $R_1$ is methyl radical and $R_2$ represents a phenylalkyl group containing from 7 to 9 carbon atoms, or a 2-indanyl group, each of which is optionally substituted on the aromatic ring by one or two alkoxy radicals containing from 1 to 4 carbon atoms, provided that $R_2$ represents alkoxy-substituted phenylalkyl when both of $X_1$ and $X_2$ represent a hydrogen or halogen atom and Y represents a hydrogen, in racemic form or in the form of optical isomers, and their addition salts with pharmaceutically acceptable mineral or organic acids.

2. A compound of the formula I of the claim 1, in which $X_1$ and $X_2$, which are identical or different, represent a hydrogen atom or a methoxy radical, their optical isomers and their addition salts with pharmaceutically acceptable acids.

3. A compound of the formula I of the claim 1, in which $R_1$ represents a methyl radical and $R_2$ represents a 3,4-dimethoxy-1-phenethyl radical, their optical isomers and their addition salts with pharmaceutically acceptable acids.

4. A compound of the formula I of the claim 1 which is 5-methoxy-3-phenyl-3-[3-(N-(3,4-dimethoxyphenethyl)-N-methylamino)-propyl]-2,3-dihydrobenzofuran, its optical isomers and its salts with pharmaceutically compatible acids.

5. A compound of the formula I of the claim 1 which is 3-phenyl-3-[3-(N-(3,4-dimethoxyphenethyl)-N-methylamino)-propyl]-2,3-dihydrobenzofuran, its optical isomers and its salts with pharmaceutically compatible acids.

6. Pharmaceutical composition useful for the treatment of a disorder requiring modulation of transmembrane and intracellular movements of calcium comprising an effective amount of a compound of claim 1 in association or admixture with an excipient or pharmaceutically-acceptable non-toxic inert carrier.

7. Method for the modulation of the transmembrane and intracellular movements of calcium in a subject in need of the same comprising the step of administering to the said subject an amount of a compound of claim 1 which is effective for the said purpose.

* * * * *

UNITED STATES PATENT AND TRADEMARK OFFICE
CERTIFICATE OF CORRECTION

PATENT NO. : 4,727,086

DATED : February 23, 1988

INVENTOR(S) : Gilbert Lavielle, Yves-Michel Gargouil and Jean-Paul Vilaine

It is certified that error appears in the above-identified patent and that said Letters Patent is hereby corrected as shown below:

Col. 2, line 49; "$x_1$," should read -- $X_1$, --

Col. 5, line 33; start a new paragraph with "The following ..."

Col. 6, line 5; "-5-]N-(3,4-" should read -- -5-[N-(3,4- --

Col. 7, line 33; "penttanol" should read -- pentanol --

Col. 8, line 25; "phoshpate:" should read -- phosphate: --

Col. 16, line EX 5b, last column in TABLE 2-continued (under "NMR") line 7; "3.86" should read -- 3.85 --

Col. 16, line EX 9b, last column in TABLE 2-continued (under "NMR") line 26; "4.22" should read -- 4.2 --

Col. 18, line EX 11, last column in TABLE 3-continued (under "NMR"), line 28; before "1.4" insert -- (base) --, "2 H;" should read -- 2H; -- and delete "11H;" (the line should now read -- (base) 1.4 ppm $\underline{m}$ 2H; --)

Col. 18, line EX 11, last column in TABLE 3-continued (under "NMR"), line 29; after "m" insert -- 11H; -- (the line should now read -- 2.2 to 2.8 ppm $\underline{m}$ 11H; --)

Col. 19, line 25; "represented" should read -- represents --

Signed and Sealed this

Twenty-seventh Day of December, 1988

*Attest:*

DONALD J. QUIGG

*Attesting Officer*   Commissioner of Patents and Trademarks